(12) United States Patent
McGovern

(10) Patent No.: US 7,955,338 B2
(45) Date of Patent: Jun. 7, 2011

(54) APPARATUS AND METHOD FOR PREPARING BONE FOR ANTI-ROTATIONAL IMPLANTATION OF AN ORTHOPEDIC ENDOPROSTHESIS

(75) Inventor: Michael A. McGovern, Wyckoff, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1065 days.

(21) Appl. No.: 11/231,587

(22) Filed: Sep. 21, 2005

(65) Prior Publication Data
US 2006/0015112 A1     Jan. 19, 2006

Related U.S. Application Data

(62) Division of application No. 10/248,565, filed on Jan. 29, 2003, now Pat. No. 7,001,392.

(51) Int. Cl.
| A61F 2/46 | (2006.01) |
| A61F 2/00 | (2006.01) |
| A61F 2/38 | (2006.01) |
| A61B 17/00 | (2006.01) |
| A61B 17/58 | (2006.01) |
| A61B 17/60 | (2006.01) |

(52) U.S. Cl. ......... 606/86 R; 606/80; 606/99; 623/20.35
(58) Field of Classification Search .............. 606/60, 606/67, 86 R, 96, 99, 104; 623/20.35; 411/322
See application file for complete search history.

(56) References Cited

U.S. PATENT DOCUMENTS

| 3,996,931 A | 12/1976 | Callender, Jr. |
| 4,187,559 A | 2/1980 | Grell et al. |
| 4,457,301 A | 7/1984 | Walker |
| 4,523,587 A | 6/1985 | Frey |
| 4,549,319 A * | 10/1985 | Meyer .......... 623/23.23 |
| 4,678,471 A | 7/1987 | Noble et al. |
| 5,053,037 A | 10/1991 | Lackey |
| 5,112,333 A | 5/1992 | Fixel |
| 5,263,955 A | 11/1993 | Baumgart et al. |
| 5,350,301 A * | 9/1994 | De Buck .......... 433/173 |
| 5,580,352 A * | 12/1996 | Sekel .......... 623/22.46 |
| 5,607,431 A | 3/1997 | Dudasik et al. |
| 5,782,925 A | 7/1998 | Collazo et al. |

(Continued)

FOREIGN PATENT DOCUMENTS
EP         257118        3/1988

(Continued)

*Primary Examiner* — Thomas C Barrett
*Assistant Examiner* — David W Bates
(74) *Attorney, Agent, or Firm* — Lerner, David, Littenberg, Krumholz & Mentlik, LLP

(57) ABSTRACT

An apparatus and method for reaming a bone, facilitating pre-implantation alignment of a prosthesis using trial components, and preparing a bone site for anti-rotational implantation of the prosthesis is provided. The apparatus includes a boring end, a mating end disposed opposite the boring end, and a keying aid disposed between the boring end and mating end. The method includes attaching a power tool to the mating end, reaming a bone canal with the boring end, detaching the power tool, attaching a trial component, conducting alignment trials, maintaining the apparatus in the desired position, detaching the trial component, cutting at least one keyway in the bone canal using a cutting device and the keying aid, removing the cutting device, removing the apparatus from the reamed bone canal, and inserting the prosthesis into anti-rotational engagement with reamed bone by aligning the key on the prosthesis with the keyway in the bone canal.

13 Claims, 3 Drawing Sheets

U.S. PATENT DOCUMENTS

| | | |
|---|---|---|
| 5,810,830 A | 9/1998 | Noble et al. |
| 5,879,394 A | 3/1999 | Ashby et al. |
| 6,117,138 A | 9/2000 | Burrows et al. |
| 6,120,504 A | 9/2000 | Brumback et al. |
| 6,126,694 A | 10/2000 | Gray, Jr. |
| 6,162,226 A * | 12/2000 | DeCarlo et al. ............ 606/80 |
| 6,174,335 B1 | 1/2001 | Varieur et al. |
| 6,179,877 B1 * | 1/2001 | Burke ................. 623/22.12 |
| 6,206,884 B1 | 3/2001 | Masini |
| 6,277,121 B1 | 8/2001 | Burkinshaw et al. |
| 6,395,004 B1 | 5/2002 | Dye et al. |
| 6,416,552 B1 | 7/2002 | Hoeppner et al. |
| 6,494,913 B1 * | 12/2002 | Huebner ............... 623/19.11 |
| 6,613,052 B1 | 9/2003 | Kinnett |
| 6,736,821 B2 | 5/2004 | Squires et al. |
| 6,824,335 B2 * | 11/2004 | Lynch ................. 408/115 R |
| 6,827,722 B1 | 12/2004 | Schoenefeld |
| 2003/0204262 A1 * | 10/2003 | Ferguson et al. ........ 623/20.15 |
| 2004/0122437 A1 | 6/2004 | Dwyer et al. |
| 2004/0267266 A1 | 12/2004 | Daniels et al. |
| 2004/0267267 A1 | 12/2004 | Daniels et al. |
| 2005/0033444 A1 | 2/2005 | Jones et al. |

FOREIGN PATENT DOCUMENTS

| | | |
|---|---|---|
| EP | 1016382 A2 | 12/1999 |
| EP | 1197182 A2 | 9/2001 |
| JP | 2003-10198 | 5/2002 |

* cited by examiner

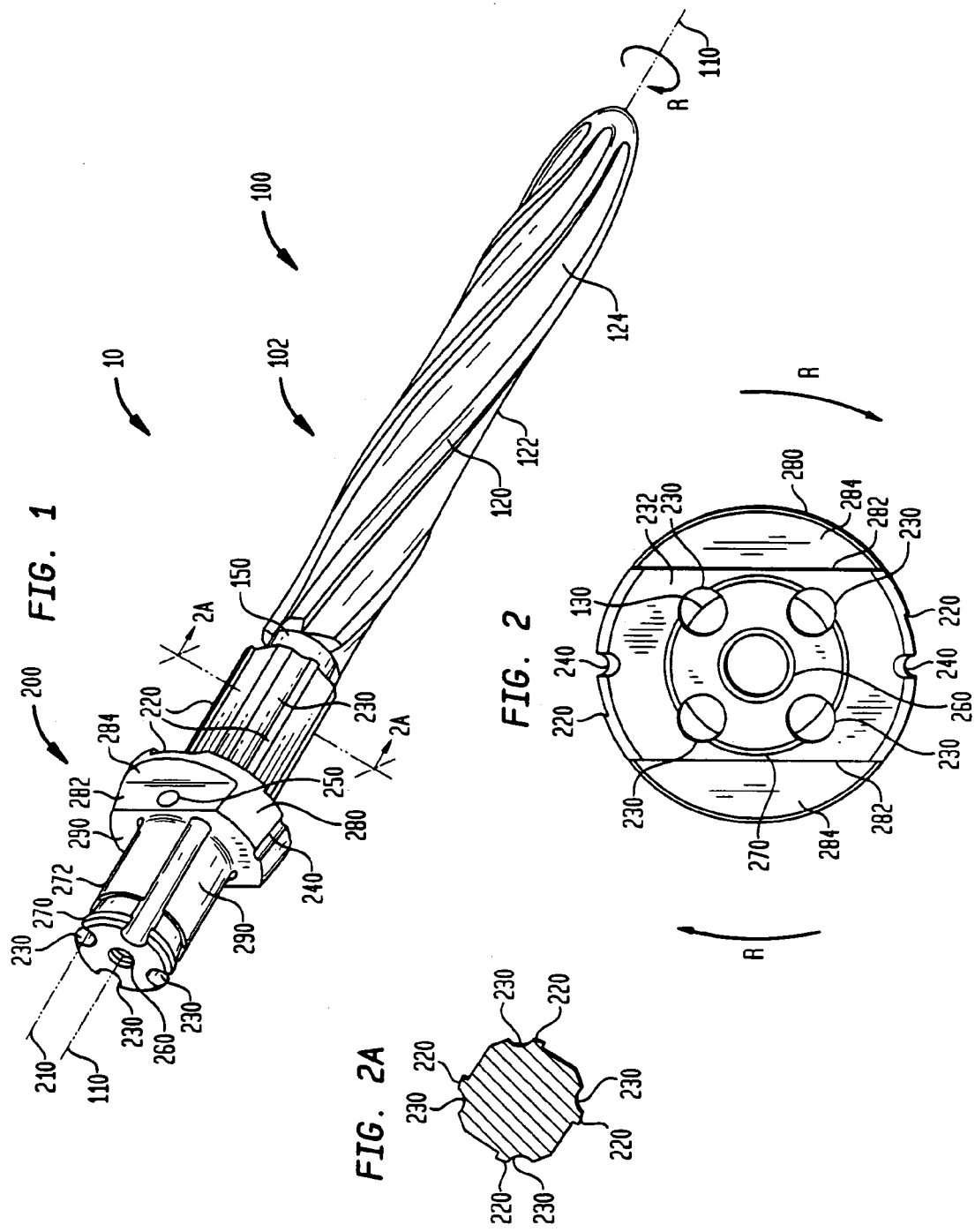

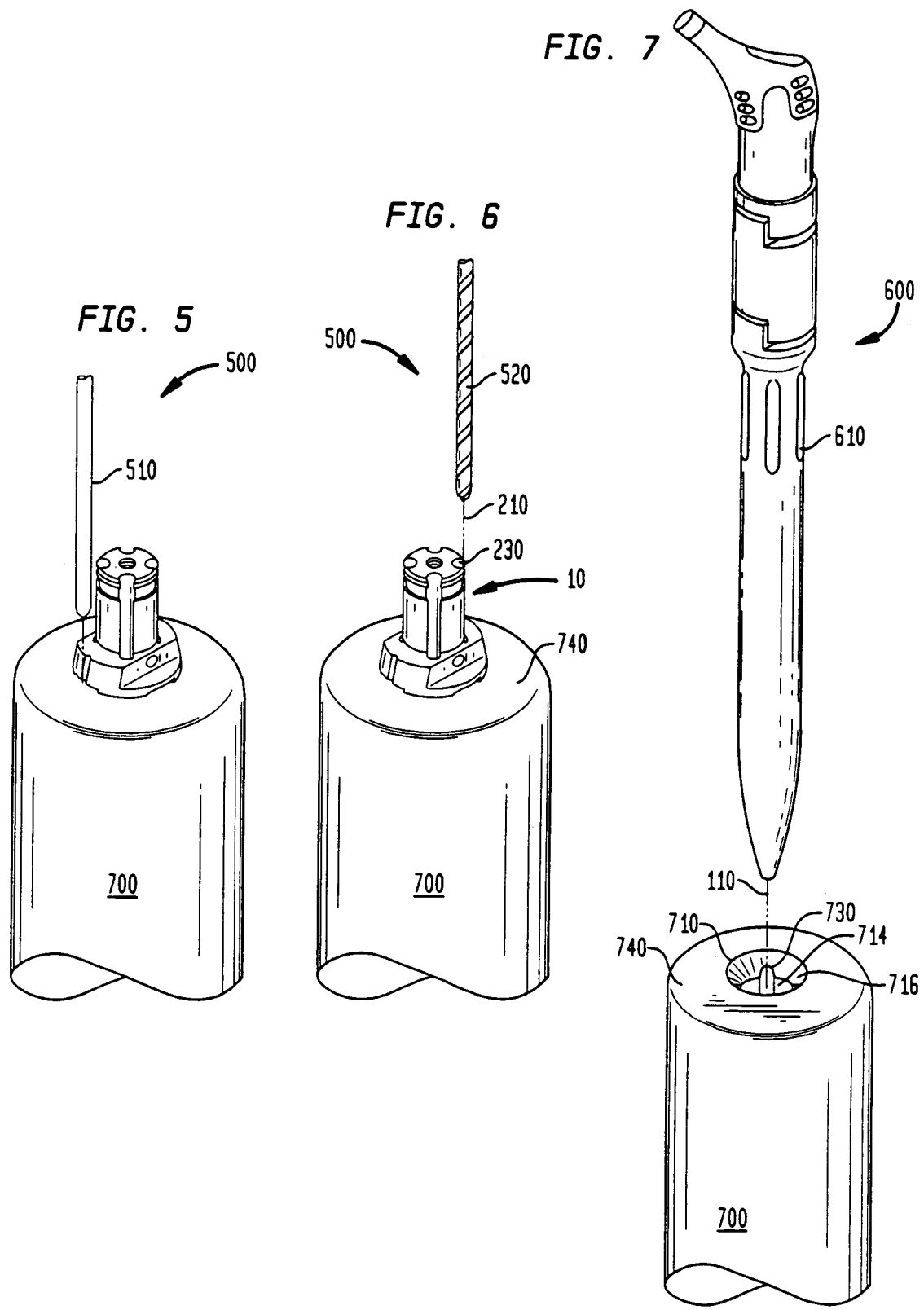

APPARATUS AND METHOD FOR PREPARING BONE FOR ANTI-ROTATIONAL IMPLANTATION OF AN ORTHOPEDIC ENDOPROSTHESIS

CROSS-REFERENCE TO RELATED APPLICATIONS

This application is a divisional of U.S. application Ser. No. 10/248,565, filed on Jan. 29, 2003, the disclosure of which is incorporated herein by reference.

BACKGROUND OF THE INVENTION

1. Field of the Invention

This invention relates to a surgical tool and method for preparing a bone site for implantation of an orthopedic endoprosthesis having anti-rotational components as well as facilitating pre-implantation alignment of the prosthesis. More particularly, the invention relates to aligning and implanting a femoral component of a total hip joint or a humeral component of a shoulder joint. However, it may also be used to align and implant femoral and tibial components of a prosthetic knee joint.

The method and surgical tool that is used to open and form the bone canal also facilitates pre-implantation alignment of the prosthesis using trial components, as well as preparation of the bone site for anti-rotational implantation of the prosthesis. Most commonly, this invention would be employed in connection with the implantation of prostheses into long bones, but it would not be limited thereto. The quantity of medical instruments, as well as the time and number of movements required in forming a bone canal and conducting pre-implantation alignment of the prosthesis using trial components is reduced with the use of this surgical tool. Also, the risk of rotational failure of the prosthesis is reduced when it is implanted into a bone canal that is shaped to accept it's anti-rotational features.

As used herein, when referring to bones or other body parts, the term "proximal" means closest to the heart, and the term "distal" means more distant from the heart. When referring to tools and instruments, the term "proximal" means closest to the practitioner, and the term "distal" means distant from the practitioner.

2. Description of Related Art

Proper alignment of orthopedic implants, such as joint replacement prostheses, is essential to the success of surgical procedures involving replacing damaged joints. Such prostheses commonly include stems for insertion into the canals of long bones. A stem is used to anchor the prosthesis in a bone cavity.

A bone cavity is commonly prepared by forming a hole in the bone, such as by drilling or reaming, and creating an opening sized and contoured to receive the stem of the prosthesis. The stem is inserted into the bone cavity, and optionally, a joint bearing member may be attached or coupled to the stem, with the joint bearing member extending out of the bone cavity.

Typically, once a stem that is coupled to a femoral component, for example, is inserted into a prepared bone cavity, it is necessary to rotate the stem to properly orient it. Sometimes, the stem must be removed and reinserted, which may damage the bone cavity and surrounding bone, as well as increase intra-operative time.

To achieve pre-implantation alignment of the prosthesis, the prosthesis stem is typically manipulated, and the desired position identified, by marking the bone and the stem. Subsequent alignment during implantation is then achieved by using the marks to align the stem with respect to the bone. The drawback to this method is the potential imprecision in the alignment. Because the marks on the stem and bone are not in close proximity to each other, parallax and other problems associated with alignment by eye may result. Also, the stem may move from its aligned position as it is inserted.

Misalignment of an implanted prosthesis in the human body is an undesirable result in joint replacement surgery. To alleviate implant misalignment, past efforts have been directed toward providing some pre-implantation trialing and marking methods that strive to achieve an implanted prosthesis having the optimal orientation.

One such effort is presented in U.S. Pat. No. 4,678,471 to Noble et al., entitled "Method and Apparatus for Preventing Rotational Failure of Orthopedic Endoprostheses". Noble et al. relates to an apparatus for making at least one groove in a medullary canal in a bone. The apparatus is an elongate member having a flattened head portion and a stem, and having one channel that receives a cutting tool for cutting a groove in the canal, remote from the resected bone surface.

Another effort is presented in U.S. Pat. No. 5,053,037 to Lackey, entitled "Femoral Instrumentation for Long Stem Surgery". Lackey relates to a bone cutting block in conjunction with a reamer, for forming the end of a long bone.

Yet another effort is presented in U.S. Pat. No. 6,206,884 to Masini, entitled "Reduction-Based Joint Replacement Apparatus and Methods". Masini relates to a reduction-based orthopedic system facilitating the installation of a properly oriented prosthetic component. Separate elements of the system for trialing and marking the bone include an anchoring unit, a trialing component, and a cutting guide.

Despite these efforts, there is still a continuing need for improving tools and methods for preparing a bone site for implantation of a prosthesis having anti-rotational components as well as facilitating pre-implantation alignment of the prosthesis.

It is therefore an object of the present invention to provide a surgical tool which facilitates reaming a bone canal, attaching and manipulating a trial component, and marking the rotational alignment of the trial component on the bone.

It is a further object of the present invention to provide a surgical tool which facilitates engagement to various tools and components for the purposes of both reaming a bone canal as well as facilitating trialing.

It is yet another object of the present invention to provide a surgical tool for cutting keyways in the bone once the rotational alignment of the trial component is determined.

SUMMARY OF THE INVENTION

These and other objects are achieved by the present invention, which is a surgical tool for reaming a bone, determining the rotational alignment of a prosthesis, and marking this alignment on the bone.

The surgical tool has a first end adapted to extend into a bone canal in a bone, a second end opposite the first end preferably adapted to engage various instruments and other tools, and at least one keying aid that is adapted to facilitate identifying the tool's orientation on a bone. The surgical tool also has a central longitudinal axis.

The first end of the tool is cylindrical and has a cross-section that is perpendicular to the longitudinal axis. In the preferred embodiment, the first end has flutes and cutting surfaces, or teeth, to shape a bone canal. The cutting teeth are intended to cut away undesired bone, while the flutes convey the cut bone out of the bone canal. It is understood, however, that other bone-removing features may be incorporated on the first end of the reamer to help prepare the bone canal for insertion of an implant. It is further noted that a set of surgical tools may be provided, each surgical tool having a differently sized cross-section. For example, a set of surgical tools having cross-sectional diameters ranging from 11 to 19 millimeters may be provided.

In the preferred embodiment, the second end of the surgical tool has a mating geometry that enables it to be engaged by various mating instruments and trial implants. For example, the second end may be engaged by a power tool, or a manual tool such as a T-handle, that would rotate the surgical tool, causing the first end to ream and remove undesired bone from the bone canal. The second end may also be engaged by a trial component used for determining the rotational alignment of a prosthesis in the bone.

In the preferred embodiment, once placed on the second end of the surgical tool, the trial component, such as a femoral component of a knee implant, may be rotated with the surgical tool in the bone canal, thereby allowing a surgeon to determine the desired orientation in which he wishes to permanently set the prosthesis. When these motions are performed in conjunction with articulation of the joint being operated upon, as is commonly known to those skilled in the art, this is referred to as "trial reduction".

Once the desired orientation is determined, the surgical tool advantageously has a combination of features or guides on the second end, that facilitate marking the bone to identify this orientation thereon so that a prosthesis may be inserted in accordance with this orientation. The combination of features includes a flange with two alignment grooves on its outer periphery, and at least one, but preferably four guide channels that penetrate the flange.

With regard to the flange, preferably one or both of the two grooves may be used as guides for a surgical marker to mark the bone after rotational alignment of the trial component has been performed. Once the bone is marked, the surgical tool may be removed from the bone canal. Thereafter, additional procedures known to those skilled in the art may be employed to further prepare the bone canal for anti-rotational implantation of a prosthesis in accordance with the marks on the bone. For example, a surgeon may manually cut out a keyway in the bone adjacent to the bone canal and, using a prosthesis having a feature, or key, corresponding to the keyway, insert the prosthesis so that it engages both the bone canal and keyway. This results in implanting the prosthesis in accordance with the mark relating to the desired position previously set by the trial component.

Alternatively, once the desired orientation for the prosthesis is determined, the trial component may be disengaged from the surgical tool while maintaining the tool's position in the bone canal. The four guide channels may then be used to shape the bone canal by forming keyways, thereby preparing the bone canal for implantation of a prosthesis having anti-rotational components, or keys.

Preferably, the four guide channels each have a longitudinal guide channel axis, as well as a cross-section, or profile, that is perpendicular to the guide channel axis. The four guide channels are advantageously located on the surgical tool such that their profiles overlap, or intersect the cross section of the first end of the surgical tool. In the preferred embodiment, the four guide channels are spaced equidistantly, equiangularly and parallel to the longitudinal axis of the surgical tool, but other variations are possible. For example, the guide channels may be oriented such that their guide channel axes are not parallel to the longitudinal axis of the surgical tool.

The guide channels are each adapted to accept a drill bit and direct the drill bit to cut anti-rotation channels, or keyways, on the periphery of the bone canal, thereby forming a non-circular bone canal cross-section. It is also recognized, however, that other tools, such as a rasp or punch, may be used in conjunction with the guide channels to form the keyways.

In the preferred embodiment, the grooves on the flange and the guide channels are preferably used in combination. The grooves are used to mark the surgical tool's orientation on the bone, and then the guide channels are used to form the keyways in the bone canal. Thereafter, the markings made by using the grooves help validate the correct positions of the keyways.

In the preferred embodiment, the distal portion of the flange that faces the first end of the surgical tool, transitions smoothly into the second end of the surgical tool via a chamfer or fillet, such that, when applied, it registers a countersink on the top surface of the bone canal. However, it is envisioned that a substantially perpendicular transition may be made as well. Therefore, according to the preferred embodiment, keyways are formed on the countersink or radius in the bone canal. Alternatively, with a flange having a substantially perpendicular transition, the keyways would be formed on the top surface of the bone canal without the countersink or radius.

Once the anti-rotation channels are formed, the surgical tool is removed from the bone canal. The prepared bone canal then receives a prosthesis having a stem with anti-rotational components, such as keys, that align with the cut keyways, and help secure the prosthesis from rotating in the bone canal.

The preferred method of using the present invention includes attaching a power tool to the second end of the surgical instrument, advancing the surgical instrument into the bone canal, disengaging the power tool from the surgical instrument, attaching a trial component to the second end of the surgical instrument, determining the desired orientation of a prosthesis by moving the trial component relative to the bone canal, marking the desired orientation on the bone with the aid of the surgical instrument, disengaging the trial component from the surgical instrument while holding the surgical instrument stationary in the bone canal, drilling keyways adjacent to the bone canal with drill bits guided by guide channels in the second end of the surgical tool, removing the surgical tool from the shaped bone canal and implanting a prosthesis having anti-rotational elements, such as keys thereon, for engaging the keyways in accordance with the desired orientation previously determined with the trial component.

BRIEF DESCRIPTION OF THE DRAWINGS

In the drawings, wherein similar reference characters denote similar elements throughout the several view:

FIG. 1 is a perspective view of the surgical tool.

FIG. 2 is a top view of the surgical tool depicted in FIG. 1.

FIG. 2A is a cross-section of the surgical tool along line 2A in FIG. 1.

FIG. 5 is a partially exploded view of a marker positioned over the surgical tool which is situated in the bone canal of the proximal femur.

FIG. 6 is a partially exploded view of a drill bit positioned over the surgical tool which is situated in the bone canal of the proximal femur.

FIG. 7 is an exploded view of a prosthesis positioned over a bone canal in the proximal femur that was formed with the surgical tool.

DETAILED DESCRIPTION

Figure 3:
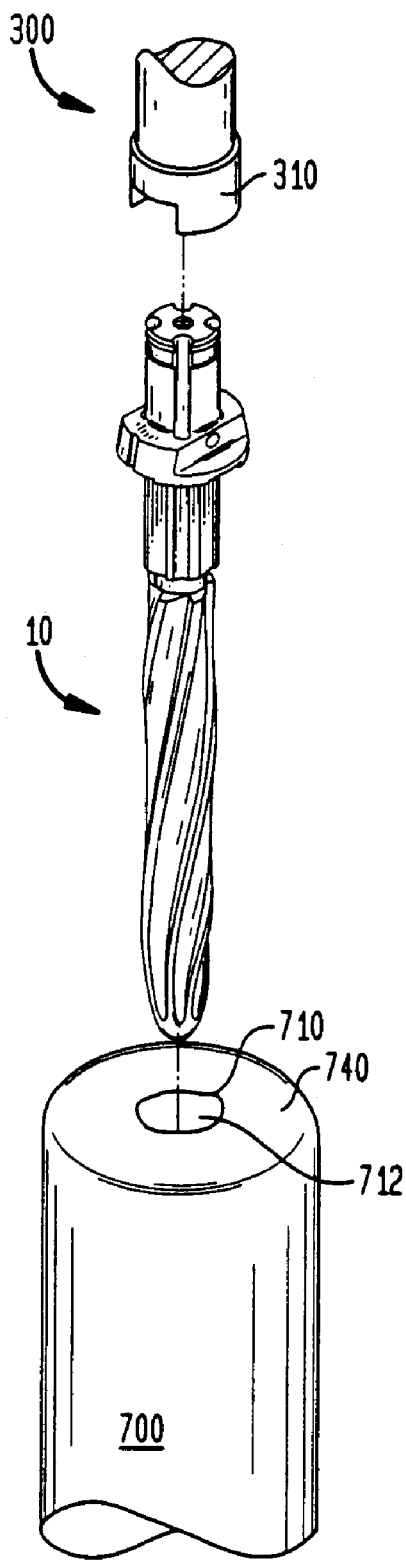
FIG. 3 is an exploded view of a driving tool, the surgical tool and a resected end of a proximal femur.

Referring to FIGS. 1 and 2, there is illustrated the surgical tool or instrument of the present invention, generally denoted as 10. In the preferred embodiment, instrument 10 has a first distal end 100 and a second proximal end 200 extending along longitudinal axis 110. First end 100 is in the form of a reamer 102 used to ream a bone canal in a long bone, while second end 200 has multiple applications including providing an attachment interface to various instruments, and providing elements facilitating marking and forming keyways in the bone. Both ends 100 and 200 of instrument 10 will be discussed in more detail, below.

With reference to FIGS. 1-3, in the preferred embodiment, reamer 102 has multiple spiraled cutting teeth 120 for reaming bone canal 710 to a desired diameter. Cutting teeth 120 form a circular cutting profile 130 that is perpendicular to longitudinal tool axis 110. Profile 130 is essentially the cutting perimeter of first end 100 of instrument 10. It is also envisioned that other forming elements may be incorporated at first end 100 of surgical instrument 10 to facilitate other common methods of preparing bone canal 710, such as features for cutting, rasping, impacting or otherwise forming bone canal 710.

Referring to FIGS. 1 and 2, reamer 102 is a standard bone reamer wherein each spiral cutting tooth 120 has a cutting edge 122 that engages the inner circumferential surface 712 of bone canal 710. When reamer 102 is rotated clockwise R, undesired bone in bone canal 710 is cut away by cutting edges 122 and conveyed out of bone canal 710, toward second end 200, via flutes, or channels 124 on reamer 102. In this manner, loose bone particles do not remain in bone canal 710 during drilling.

In the preferred embodiment, as best seen in FIG. 1, between reamer 102 and flange 280, is a circumferential series of cutting teeth 220 and guide channels 230. Straight cutting teeth 220 run substantially from the end of spiraled teeth 120 up to the bottom of flange 280. These straight cutting teeth 220 further facilitate shaping bone canal 710. Four guide channels 230 are formed intermediate the straight cutting teeth 220, although it is recognized that at least one guide channel would suffice. Since guide channels 230 are straight, cutting teeth 220 must also be straight, as opposed to spiraled, so that guide channels 230 do not have interruptions in their lengths.

A recessed transition portion 150 is provided as a separation between spiraled teeth 120 and straight teeth 220. This is primarily for machining purposes. It is understood, however, that various other transition configurations may exist for this purpose.

Proximal of cutting teeth 220, second end 200 includes flange 280 which, in the preferred embodiment, has a generally cylindrical shape centered about longitudinal axis 110. The distal portion of flange 280 that faces first end 100 of surgical tool 10, transitions smoothly into second end 200 via a chamfer or fillet, such that, as shown in FIG. 7, it registers a countersink or radius 716 on top surface 740 of bone canal 710.

Flange 280 further has two oppositely oriented substantially flat surfaces 282 extending parallel to axis 110 and two radially extending mating surfaces 284 positioned perpendicularly to axially extending surfaces 282. As best seen in FIG. 1, second end 200 also has a cylindrical surface 290 terminating in an annular mounting recess 272, and an annular mounting lip 270 just above recess 272. Lip 270, recess 272, and surfaces 282 and 284 provide features and surfaces for engaging, or facilitating the mounting of, various instruments such as driving tools and trial components, which will be discussed in more detail, below. Numerous alternative configurations and features, however, are also envisioned. Additionally, a counter-rotation hole 250, and a retraction hole 260, both located on the second end 200 of instrument 10, are provided, and will be discussed in more detail, below. Moreover, it is recognized that while having any of the features of second end 200 described herein, second end 200 may also be shaped, at least in part, as a trial component.

Flange 280 further has oppositely oriented alignment marking grooves 240 on its periphery. These grooves 240 may be used to mark the rotational orientation, or position of instrument 10, on resected bone surface 740 of bone 700.

In the preferred embodiment, second end 200 of instrument 10 also has four peripherally located guide channels 230 that run distally along surface 290 of second end 200, penetrate flange 280, and terminate at transition portion 150. With particular reference to FIG. 2A, preferably each guide channel 230 has a circular profile 232 which is perpendicular to a guide channel axis 210, and at least in the area of teeth 220 distal of flange 280, is partially open. As seen in FIG. 2, each guide channel 230 is oriented on instrument 10 such that guide channel axis 210 is substantially parallel to longitudinal tool axis 110, and profile 232 intersects cutting profile 130, i.e., the full circular profile 232 of each channel 230 extends beyond the diameter of profile 130. However, other configurations of guide channel axes relative to the longitudinal tool axis are also envisioned. As will be explained in more detail below, the intersecting profiles on instrument 10 facilitate forming a cylindrical bone canal having anti-rotation keyways.

Guide channels 230 are shown in FIGS. 1 and 2 as being equidistantly and equiangularly spaced apart from each other, however it is envisioned that other geometric configurations are conceivable as well. In addition, as few as one channel can be used. As will be discussed below in more detail, grooves 240, as well as guide channels 230, are used to the mark the rotational position of instrument 10 on resected bone surface 740, and guide channels 230 may be further used to form keyways in bone canal 710 in order to prepare it to receive an implant having complimentary anti-rotational elements, or keys, formed thereon.

Referring to FIG. 3, instrument 10 is shown positioned over an unreamed bone canal 710 in a bone section such as the resected proximal femur 700. It is recognized, however, that the bone section may also be a distal femur, or an end of the tibia or humerus. Above instrument 10 is the driver interface portion 310 of a driving tool, or driver 300 such as a manual or power drill. In operation, driver interface 310 of driver 300 engages instrument 10 at end 200 via mounting lip 270, mounting recess 272, vertical mating surfaces 282 and horizontal mating surfaces 284. Such an engagement of parts facilitates controlled manipulation of instrument 10. Specifically, if driver 300 is a drill, then clockwise R rotation of driver 300 translates through second end 200 into rotation of reamer 102, thereby causing first end 100 of instrument 10 to shape bone canal 710.

Figure 4:
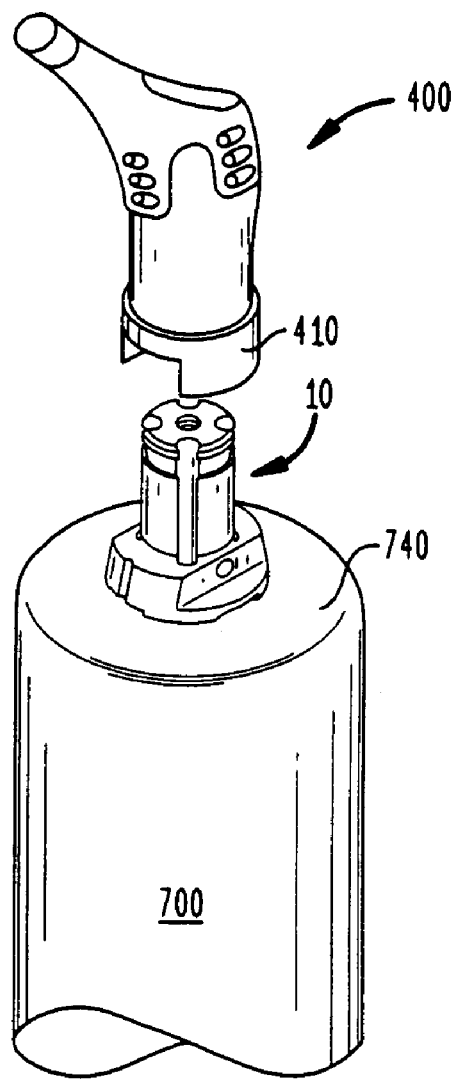
FIG. 4 is a partially exploded view of a trial component positioned over the surgical tool which is situated in the bone canal of the proximal femur.

With reference to FIG. 4, once bone canal 710 has been reamed, and the underside of flange 280 of instrument 10 is in flush contact with resected bone surface 740, driver 300 is disengaged from proximal second end 200. At this point, without removing instrument 10 from bone canal 710, a trial component, such as the one depicted by hip joint element 400, may be placed on second end 200. In the preferred embodiment, trial component 400 has a similar interface configuration 410 as the interface 310 of driver 300, and mates similarly with second end 200.

While engaged to second end 200, trial component 400 and instrument 10 may be freely rotated to any position, and trial reduction may be performed. This allows a surgeon to determine the optimal orientation of trial component 400 for implantation into proximal femur 700 in view of the actual expected function of a prosthesis in the hip joint.

Referring to FIGS. 5-7, once the optimal orientation of trial component 400 is set, this position may be marked on proximal femur 700 in at least one of two ways. In one approach, without disengaging trial component 400 from second end 200, a marking instrument 500, such as a marker 510, may be set against groove 240 on flange 280 of instrument 10, and used to mark resected bone surface 740. Optionally, both grooves 240 may be used to make such marks on bone surface 740. These marks identify the desired rotational orientation in which implant 600 should be implanted into proximal femur 700. Alternately, marking may be done by using the drill bit 520 of FIG. 6, which may be guided along grooves 240 to make indentations (not shown) in resected bone surface 740. Once the marks are made on bone surface 740, instrument 10 may be removed from bone canal 710, and further preparatory measures may be implemented in accordance with procedures known to those skilled in the art, for preparing the marked implant site for anti-rotational implantation of implant 600.

Alternatively, once the optimal orientation of trial component 400 is set, while keeping instrument 10 in its determined rotational position in bone canal 710, trial component 400 is disengaged from second end 200 of instrument 10. Drill bit 520 is then attached to a drill (not shown), inserted into at least one guide channel 230, and used to drill at least one keyway 730 on the periphery of bone canal 710. It is also recognized, however, that other tools, such as a rasp or punch, may be used in conjunction with the guide channels to form the keyways. Straight and uninterrupted guide channels 230 advantageously facilitate insertion and controlled manipulation of drill bit 520 during this process.

In the preferred embodiment, the grooves on the flange and the guide channels are used in combination. The grooves are used to mark the surgical tool's orientation on the bone, and then the guide channels are used to form the keyways in the bone canal. Thereafter, the markings made by using the grooves help validate the correct positions of the keyways.

In order to prevent instrument 10 from rotating in bone canal 710 while anti-rotational channels 730 are being drilled, there is provided a counter-rotation hole 250 on instrument 10. Counter-rotation hole 250 penetrates instrument 10 through flange 280, substantially perpendicularly to longitudinal tool axis 110, and in between vertical mating surfaces 282. During the drilling of channels 730, a bar or tool (not shown) may be inserted into hole 250, and held in position to prevent instrument 10 from rotating.

Once anti-rotation channels 730 are prepared, drill bit 520 may be removed from instrument 10. To assist in removing instrument 10 from bone canal 710, there is optionally provided a threaded retraction hole 260 on second end 200 of instrument 10. A tool (not shown) may be threadably inserted into hole 260, and then used to facilitate the retraction of instrument 10 from bone canal 710. The result of the reaming and drilling process described by the second approach herein, is a bone canal 710 having a countersink 716, smooth circumferential canal surface 714, and at least one keyway 730. It is understood, however, that if the transition between flange 280 and second end 200 is substantially perpendicular, the keyway 730 would be formed on top surface 740 of bone canal 710 without countersink 716.

Now that the forming of bone canal 710 has been completed, an implant such as the one depicted in FIG. 7 by element 600, having anti-rotational components, or keys 610, may be implanted into bone canal 710 according to the previously measured, marked and machined orientations of keyways 730. The mating of keys 610 with keyways 730, on the periphery of bone canal 710, helps prevent the rotation of implant 600 about its axis 110 within bone canal 710 after implantation.

Instrument 10, as taught herein, is used to prepare an intramedullary bone canal 710 in the proximal femur 700 for anti-rotational implantation of implant 600. However, it is noted that in a variety of sizes, instrument 10 and the methods for its use, may be implemented on other joints for similar procedures. For example, the distal femur, tibia and the proximal humerus may be prepared in a similar manner to accept a prosthesis for interaction with the knee or shoulder joint, respectively.

Although the invention herein has been described with reference to particular embodiments, it is to be understood that these embodiments are merely illustrative of the principles and applications of the present invention. It is therefore to be understood that numerous modifications may be made to the illustrative embodiments, and that other arrangements may be devised, without departing from the spirit and scope of the present invention as defined by the appended claims.

The invention claimed is:

1. A method of preparing a bone for insertion of a prosthesis, said method comprising:
    forming a bone canal in a bone utilizing a surgical instrument, the surgical instrument having distal and proximal ends, the distal end including a reaming portion having a first longitudinal axis and the proximal end including at least one guide borehole having a second longitudinal axis parallel and offset to the first longitudinal axis;
    forming at least one anti-rotation recess in said bone along the second longitudinal axis, said at least one anti-rotation recess having a longitudinal axis coaxial with the second longitudinal axis and having a channel profile that is perpendicular to first and second longitudinal axes of the surgical instrument;
    engaging a trial component having a joint connection element to said surgical instrument;
    implanting the surgical instrument into said bone canal;
    moving said trial component while said trial component is engaged to said surgical instrument, and while said surgical instrument is maintained in said bone canal, to determine an implanting position for said prosthesis;
    marking said implanting position on said bone by using said surgical instrument as a guide;
    removing said surgical instrument engaged to said trial component from said bone canal; and
    implanting said prosthesis in said marked implanting position in said bone.

2. The method of claim 1 further comprising attaching a power tool to said surgical instrument to facilitate forming said bone canal in said bone.

3. The method of claim 1 wherein moving said trial component comprises performing trial reduction.

4. The method of claim 1 further comprising forming said at least one anti-rotation channel such that said channel profile intersects said bone canal.

5. The method of claim 1 wherein said prosthesis has a key, and implanting said prosthesis in said marked implanting position in said bone comprises aligning said key with said at least one anti-rotation channel and inserting said prosthesis in said channel such that said key engages said anti-rotation channel.

6. The method of claim 1 wherein marking said implanting position on said bone comprises utilizing said surgical instrument in forming multiple anti-rotation channels in said bone adjacent to said bone canal, each of said multiple anti-rotation channels having a channel axis and a channel profile that is perpendicular to said channel axis.

7. The method of claim 6 further comprising forming said multiple anti-rotation channels such that each of said channel profiles intersects said bone canal.

8. The method of claim 6 further comprising forming said multiple anti-rotation channels such that each of said multiple channels is substantially parallel to said bone canal.

9. The method of claim 6 further comprising forming said multiple anti-rotation channels such that each of said channel profiles intersects said bone canal and each of said multiple channels is substantially parallel to said bone canal.

10. A method of preparing a bone for insertion of a prosthesis, said method comprising:
    forming a bone canal in a bone utilizing a surgical instrument having distal and proximal ends, the distal end including a reaming portion having a first longitudinal axis and the proximal end including at least one guide borehole having a second longitudinal axis parallel and offset to the first longitudinal axis;
    forming at least one anti-rotation recess in said bone along the second longitudinal axis, said at least one anti-rotation recess having a longitudinal axis coaxial with the second longitudinal axis and having a channel profile that is perpendicular to first and second longitudinal axes of the surgical instrument;
    implanting a surgical instrument into said bone canal;
    engaging a trial component having a joint connection element to said surgical instrument;
    performing trialing using said surgical instrument to determine an implanting position;
    marking said implanting position on said bone by using said surgical instrument as a guide;
    removing said surgical instrument engaged to said trial component from said bone canal; and
    implanting said prosthesis in said marked implanting position in said bone.

11. The method of claim 10 wherein forming said bone canal is performed by reaming said bone.

12. The method of claim 10 wherein performing trialing comprises performing trial reduction.

13. The method of claim 10 wherein marking said implanting position on said bone includes utilizing said surgical instrument in forming multiple anti-rotation channels in said bone adjacent to said bone canal.

* * * * *